United States Patent [19]

Gittos

[11] Patent Number: 4,738,973
[45] Date of Patent: Apr. 19, 1988

[54] PHARMACEUTICAL COMPOSITIONS AND MEDICAL USES OF DIOXOPIPERIDINE DERIVATIVES

[75] Inventor: Maurice W. Gittos, Plobsheim, France

[73] Assignee: National Research Development Corporation, London, England

[21] Appl. No.: 905,525

[22] Filed: Sep. 10, 1986

[30] Foreign Application Priority Data

Sep. 11, 1985 [GB] United Kingdom ............... 8522455
Feb. 17, 1986 [GB] United Kingdom ............... 8603909
Feb. 17, 1986 [GB] United Kingdom ............... 8603910

[51] Int. Cl.$^4$ .......................................... A61K 31/445
[52] U.S. Cl. ................................................. 514/328
[58] Field of Search ...................................... 514/328

[56] References Cited

U.S. PATENT DOCUMENTS 3,963,729 6/1976 Gittos ........................... 260/293.86
4,461,771 7/1984 Gittos ................................. 514/328

OTHER PUBLICATIONS

Gray, J. A., The Neuropsychology of Anxiety, Clarendon Press (1982) pp. 399–407 British National Formulary (7th edition, 1984), pp. 128–135 and 144–151.
The Extra Pharmacopoeia, Martindale, pp. 1504–1563 & pp. 110–134 (28th ed.).
Liebowitz et al., Psychopharmocology Bulletin, vol. 17 (1983), 159–160.
Briley et al., Brit. J. Pharma. 1986, 87, 217p.
Lydiard et al., Am J Psychiatry, vol. 144 (1987), 5, 664–5.
Chem. Abst. 81-120488j (1974).
Conn's Current Therapy, 1986, pp. 924–925.
Liebowitz et al., J. Clin. Psychopharm. vol. 6, 1, 13–20.
Breier et al., Atch Gen Psychiatry, vol. 41, Dec. 1984, p. 1129.
Liebowitz et al., Psychopharmacology Bulletin, vol. 22 (1986), 3, 792–796.
Clerc et al., Am. J. Psychiatry, 143:2, Feb. 1986.
Brogden et al., Drugs (1981) 21, 415–417.

*Primary Examiner*—Stanley J. Friedman
*Attorney, Agent, or Firm*—Cushman, Darby & Cushman

[57] ABSTRACT

Phenyl-3-aminoalkyl-4-methyl-2,6-dioxopiperidines of the Formula I

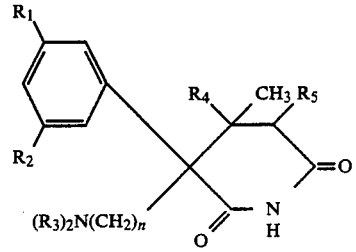

wherein:
$R_1$ represents methoxy, ethoxy or hydroxy,
$R_2$ represents methoxy, ethoxy, hydroxy or hydrogen;
each $R_3$ independently represents methyl or ethyl;
$R_4$ represents hydrogen or methyl;
$R_5$ represents hydrogen or methyl; and
n represents 2 or 3, and a pharmacologically acceptable acid addition salt thereof (a) have anxiolytic activity, (b) antagonize the anxiogenic activity of benzodiazepine inverse agonists, (c) reduce chronic abnormally high brain levels of serotonin or its metabolite 5-hydroxy-indoleacetic acid and (d) have antibacterial and antiviral activity. These activities are believed to be related to a reduction in serotonin turnover caused by blocking the depolarization activation of tryptophan hydroxylase. Novel compositions comprise the compounds with a benzodiazepine agonist or benzodiazepine inverse agonist.

4 Claims, No Drawings

PHARMACEUTICAL COMPOSITIONS AND MEDICAL USES OF DIOXOPIPERIDINE DERIVATIVES

The invention relates to the treatment of anxiety and other medical conditions with certain 3-phenyl-3-aminoalkyl-4-methyl-2,6-dioxopiperidines and to the co-administration of said compounds with benzodiazepine agonists or with benzodiazepine inverse agonists. The invention provides pharmaceutical compositions containing said dioxopiperidine compounds, the use of the compounds in the manufacture of medicaments for the treatment of anxiety or other medical conditions, and methods of treatment of anxiety or other medical conditions using the compounds.

The most widely prescribed anti-anxiety drugs are benzodiazepines angonists and it is known that these drugs act by interacting with a benzodiazepine receptor. When used in low doses they have virtually no side effects but their anti-anxiety effectiveness is often not sufficient. Increasing the dose to a normal effective one often produces side effects such as dizziness and sedation. These doses can also lead to memory impairment. Further, tolerance to their effect usually develops within four months of continuous use and there exists a substantial risk of addiction in many patients The benzodiazepine agonists include benzodiazepine derivatives which can produce 50% inhibition of tritiated flunitrazepam binding at a benzodiazepine receptor at a concentration less than $10^{-5}$ molar, and which produce anticonvulsant effects in animals which are subject to blockade by the benzodiazepine antagonist RO 15-1788. Prominent among the benzodiazepine agonists are chlorodiazepoxide (i.e. 7-chloro-2-methylamino-5-phenyl-3H-1,4-benzodiazepine-4-oxide), diazepam (i.e. 7-chloro-1,3-dihydro-1-methyl-5-phenyl-2H-1,4-benzodiazepin-2-one), bromazepam (i.e. 7-bromo-1,3-dihydro-5-(2-pyridyl)-2H-1,4-benzodiazepin-2-one), prazepam (i.e. 7-chloro-1-(cyclopropylmethyl)-1,3-dihydro-5-phenyl-2H-1,4-benzodiazepin-2-one), oxazepam (i.e. 7-chloro-1,3-dihydro-3-hydroxy-5-phenyl-2H-1,4-benzodiazepin-2-one), medazepam (i.e.7-chloro-2, 3-dihydro-1-methyl-5-phenyl-1H-1,4-benzodiazepine), lorazepam (i.e. 7-chloro-5-(2-chlorophenyl)-1,3-dihydro-3-hydroxy-2H-1,4-benzodiazepine-2-one), clorazepate (i.e. 7-chloro-2,3-dihydro-2-oxo-5-phenyl-1H-1,4-benzodiazepine-3-carboxylic acid), flunitrazepam (i.e. 5-(2-fluorophenyl)-1,3-dihydro-1-methyl-7-nitro-2H-1,4-benzodiazepine-2-one), nitrazepam (1,3-dihydro-7-nitro-5-phenyl-2H-1,4-benzodiazepine-2-one), and clobazam (i.e. 7-chloro-1-methyl-5-phenyl-1H-1,5-benzodiazepine-2,4-(3H,5H)-dione).

Specific benzodiazepine antagonists have become available which have intrinsic pharmacological properties that are opposite to those of the benzodiazepine agonists and which are referred to as "benzodiazepine inverse agonists". These inverse agonists enhance the performance of animals in learning and memory tests and it is believed that they could be of use in the treatment of senile dementia and Alzheimers disease. However, they are anxiogenic both in animals and man and this limits their usefulness.

The benzodiazepine inverse agonists include compounds which can produce 50% inhibition of flunitrazepam binding at a benzodiazepine receptor at a concentration less than $10^{-5}$ molar and which produce proconvulsant or convulsant effects in animals which are subject to blockade by the benzodiazepine antagonist RO 15-1788. Predominant among the benzodiazepine inverse agonists are methyl beta-carboline-3-carboxylate, ethyl beta-carboline-3-carboxylate, methyl 6,7-dimethoxy-4-ethyl-betacarboline-3-carboxylate and 3-methylaminocarbonylbeta-carboline.

Benzodiazepine agonists and inverse agonists are generally believed to exert their respective anxiolytic or anxiogenic actions by respectively enhancing or reducing the coupling function of the benzodiazepine receptor to the gamma-aminobutyric acid (GABA) receptor-chloride channel complex. It is also known that benzodiazepine agonists reduce the turnover of serotonin (5-hydroxytryptamine; 5HT) but the significance of this reduction has not previously been known.

It is known that the brain levels of 5HT and/or its metabolite 5-hydroxy indoleacetic acid (5HIAA) are abnormally high in certain affective disorders. Examples of such disorders are the Kleine-Levin syndrome (Koerber R.K. et al Neurology 1984, 34, 1597–1600), serotonin-irritation syndrome (Gianniani A.J. et al J. Clin. Psychiatry, 44, 262–4 (1983); Krueger A.P. et al, Science, 1976, 1209) and sleep apnea (Barruzzi, A. et al Sleep 3, 247–9 (1980); Mangin P. et al Adv. Biosci. 21, 217–9 (1979); Cromer, H. et al J. Neurol. Neurosurg. Psychiatry 44, 1165–7 (1981)).

It is known that 5HT activation depresses respiration (Lundberg D.B.A. et al J. Pharm. Exp. Therap. 212 397–404 (1980) and it has been suggested that the abnormally high brain levels of 5HT are responsible for the disorders of the Kleine-Levin and sleep apnea syndrome and sudden infant death (Koerber R.K. et al supra). The same workers have proposed that the 5HT excess could be controlled by the elimination of tryptophan-containing foods from the diet. Such a diet could however cause problems because tryptophan is normally incorporated into many essential peptides and proteins. The brain levels of 5HT also can be diminished by blocking the transformation of tryptophan into 5-hydroxy tryptophan (5HTP) This can be accomplished by the use of the known tryptophan hydroxylase inhibitor para-chlorophenylalanine (PCPA) but the continued use of this inhibitor is precluded because of its untoward toxic effects Serotonin-irritation syndrome is a condition associated with high cation environments, such as hot dry winds (eg. Fohn and Khansin winds), high-tension cables and waterfalls. It is believed that anions increase degradation of 5HT and that the cations in a high cation environment reduce this degradation by neutralizing anions and thereby increase 5HT levels (Krueger et al supra).

Further, the strength of the immune response is known to be modulated by 5HT acting via peripheral (ie. non-brain) mechanisms (Jackson, J. C. et al Immunology 54, 505–512 (1985). Thus systemic administration of 5HT or its precursor 5-hydroxytryptophan (5HTP) to mice supresses the normal immune response to an antigen challenge. Conversely, the known tryptophan hydroxylase inhibitor para-chlorophenylalanine (PCPA) enhances the normal immune response.

It has been disclosed in GB 1455687 (also AU 480855, BE 808958, DE 2363052.6, FR 7346904, JP 6053014 and US 3,963,729) that inter alia 3-phenyl-3-aminoalkyl-4-methyl-2,6-dioxopiperidine derivatives of the following Formula I have central nervous system, especially antidepressant, activity:

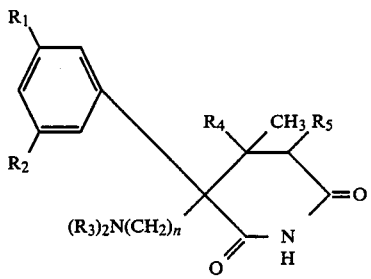

wherein:
R$_1$ represents methoxy, ethoxy or hydroxy,
R$_2$ represents methoxy, ethoxy, hydroxy or hydrogen;
each R$_3$ independently represents methyl or ethyl;
R$_4$ represents hydrogen or methyl;
R$_5$ represents hydrogen or methyl; and
n represents 2 or 3.

The specific examples of compounds of Formula I stated in the US Patent are 3-(3'-methoxyphenyl)-3-(3"-N,N-dimethylaminopropyl)-4,4-dimethyl-2,6-dioxopiperidine; 3-(3'-methoxyphenyl)-3-(2"-N,N-dimethylaminoethyl)- 4,4-dimethyl-2,6-dioxopiperidine; 3-(3'-methoxyphenyl)-3-(3"-N,N-dimethylaminoethyl)-4-methyl-2,6-dioxo-piperidine; and 3-(3'-methoxyphenyl)-3-(3"-N,N-dimethylaminoethyl)-4,5-dimethyl-2,6-dioxopiperidine.

It has recently been disclosed in U.S 4,461,771 that compounds of Formula I in which R$_4$ represents methyl and R$_5$ represents hydrogen reduce in vitro the activity of tryptophan hydroxylase by blocking the depolarization-induced activation of the enzyme in the brain stem and hence are of potential use in the prophylactic treatment of the stressful disorder migraine. More recently, it has been established that at least one compound of Formula I (viz 3-(3'-methoxyphenyl)-3-(3"-N,N-dimethylaminopropyl)-4,4-dimethyl-2,6-dioxopiperidine; AGN 2979) also blocks in vitro the activation of tryptophan hydroxylase resulting from exposure of brain stem slices to metabolic inhibitors or methylxanthines or induced by incubation of supernatant preparations of the enzyme under phosphorylating conditions (Boadle-Biber, M. C. et al Biochem. Pharmacol. 35, 1521–6, (1986)). However, AGN 2979 has no significant effect in vitro upon the unactivated enzyme (Boadle-Biber, M. C. et al supra).

It has now surprisingly been found that the compounds of Formula I have anxiolytic activity apparently without having any affinity for, or exerting any action at, the benzodiazepine receptor. The Inventor believes that this activity is caused by a reduction of the turnover of 5HT resulting from inhibiting the activity of tryptophan hydroxylase and indicates that 5HT turnover is an important factor in the action of anxiolytics and anxiogenics. Accordingly, the compounds are of use in the treatment of anxiety and further in the reduction of addiction to benzodiazepine agonists (by co-administration to gradually reduce benzodiazepine doses) and the antagonism of the anxiogenic effect of benzodiazepine inverse agents.

According to a first aspect of the present invention therefore, there is provided a method of treating a patient suffering from anxiety which comprises administering to the patient an anti-anxiety effective amount of a compound of Formula I or a pharmaceutically acceptable salt thereof.

According to a second aspect, the present invention provides the use of a compound of Formula I or a pharmaceutically acceptable salt thereof in the manufacture of a medicament for the treatment of anxiety.

The anxiolytic activity of the compounds of Formula I can be assessed by observing the exploratory activity of rats in the elevated plus-maze method of Pellow and File (Pharmacol Biochem Behav. 24, 525–529 (1986)).

As indicated above, the pharmacological mechanism for the anxiolytic activity of the compounds of Formula I is believed to be due to their action in blocking the depolorisation activation of tryptophan hydroxylase resulting in a reduction in 5HT turnover. This reduction can be measured by the method of Neff, Tozer and Brodie described by Sugrue et al (European J. Pharmacol 40, 121–30 (1976). As an illustration an ip dose of 10 mg/kg of AGN 2979 reduces the hourly turnover of 5HT in rats by 90%. The compounds of Formula I can be administered in various manners to achieve the desired anxiolytic effect. The compounds can be administered alone or in the form of pharmaceutical preparations to the patient being treated either orally or parenterally, for example subcutaneously or intravenously. The amount of compound administered will vary and can be any anti-anxiety effective amount. Depending upon the patient and the mode of administration, the quantity of compound administered may vary over a wide range to provide from about 0.1 mg/kg to 20 mg/kg*, usually 0.5 mg/kg to 10 mg/kg, of body weight of the patient per dose. Unit doses of these compounds can contain, for example from about 10 mg to 500 mg usualy 10 to 100 mg of the compound and may be administered for example from 1 to 4 times daily.

The compounds of Formula I have virtually no action at benzodiazepine receptors. The capacity of a selected number of compounds of Formula I to displace triturated flunitrazepam from benzodiazepine receptors has been measured with the results set forth in Table I below:-

TABLE 1

| | COMPOUND OF FORMULA I | | | | |
|---|---|---|---|---|---|
| | 2979 | 3222 | 2939 | 3181 | *DIAZEPAM |
| IC$_{50}$(uM) [$^3$H]Flunitrazepam Binding | 350 | 1300 | 9000 | 6700 | 0.014 |

*7-chloro-1,3-dihydro-1-methyl-5-phenyl-2H—1,4-benzodiazepine-2-one

The absence of action at benzodiazepine receptor makes the compounds of Formula I particularly useful for co-administration with benzodiazepine agonists because the compounds appear to exert their anxiolytic activities by different routes.

Thus, in a third aspect, the present invention provides an anxiolytic pharmaceutical composition comprising a benzodiazepine agonist and a compound of Formula I or a pharmaceutically acceptable salt thereof.

A fourth aspect of the present invention provides a pack comprising a quantity of a pharmaceutically acceptable dosage form of a benzodiazepine agonist and, separately therefrom, a quantity of a compound of Formula I or a pharmaceutically acceptable salt thereof.

A fifth aspect of the present invention provides a method for treating anxiety in a patient which comprises administering to the patient in combination therapy a benzodiazepine agonist and a compound of Formula I or a pharmaceutically acceptable salt thereof.

The combination therapy allows low, well tolerated, doses of the benzodiazepine agonist to be used (with their accompanying sedative effect) to produce an extremely effective combined sedative and anxiolytic action better than that achieved with high doses of the benzodiazepine alone. The combination apparently is extremely well tolerated without any distressing side effects. This aspect of the invention has particular application to the treatment of psychotic depressives who suffer from both anxiety and depression and have problems going to sleep.

The two active compounds can be administered in various manners to achieve the desired effect. They can be administered alone or in the form of pharmaceutical preparations to the patient being treated either orally or parenterally, for example subcutaneously or intravenously. The amount of compound administered will vary and can be any effective anxiety relieving amount.

The dosage will, of course, vary according to the ratio of combination of benzodiazepine agonist and compound of Formula I employed, mode of administration, patient and therapy desired. In general a suitable daily dose of the dioxopiperidine derivatives of Formula I is from 50 to 700 mg, preferably 150 to 500 mg. The potencies of the benzodiazepine agonists vary and therefore an indicated weight ratio of dioxopiperidine to benzodiazepine can be from 400:1 to 4:1. Conveniently, however, the dose of the benzodiazepine is from about 5 to 50% of the daily dose for the anxiety indication.

The daily dosage may be conveniently administered 2 to 4 times a day in divided doses or once or twice a day in sustained release form. The benzodiazepine agonist and dioxopiperidine may be combined in a single dosage form or retained separately until required for concomitant administration.

The absence of action at benzodiazepine receptors also makes the compounds of Formula I particularly useful for co-administration with benzodiazepine inverse agonists to antagonize the anxiogenic activity thereof and hence extend their usefulness to treat senile dementia and Alzheimer's disease.

Thus, in a sixth aspect, the invention provides a pharmaceutical composition comprising a benzodiazepine inverse agonist and a compound of Formula I or a pharmaceutically acceptable salt thereof.

A seventh aspect of the invention provides a pack comprising a quantity of a pharmaceutically acceptable dosage form of a benzodiazepine inverse agonist and, separately therefrom, a quantity of a pharmaceutically acceptable dosage form of a compound of Formula I or a pharmaceutically acceptable salt thereof.

A eighth aspect of the present invention provides a method for treating senile dementia or Alzheimer's disease in a patient which comprises administering to the patient in combination therapy a benzodiazepine inverse agonist and a compound of Formula I or a pharmaceutically acceptable salt thereof.

The two active compounds can be administered in various manners to achieve the desired effect. They can be administered alone or in the form of pharmaceutical preparations to the patient being treated either orally or parenterally, for example subcutaneously or intravenously.

The dosage will, of course, vary according to the ratio of combination of benzodiazepine inverse agonist and compound of Formula I employed, mode of administration, patient and therapy desired. In general a suitable daily dose of the dioxopiperidine derivatives of Formula I is from 50 to 700 mg, preferably 150 to 500 mg. The potencies of the benzodiazepine inverse agonists vary and therefore an indicated weight ratio of dioxopiperidine to benzodiazepine inverse agonist can be from 200:1 to 4:1.

The daily dosage may be conveniently administered 2 to 4 times a day in divided doses or once or twice a day in sustained release form. The benzodiazepine inverse agonist and dioxopiperidine may be combined in a single dosage form or retained separately until required for concomitant administration.

It also has unexpectedly been found that the compounds of Formula I can diminish the brain levels of 5HT and 5HIAA under normal conditions and are of use in the treatment of disorders associated with abnormally high levels of 5HT in the brain such as Kleine-Levin, sleep apnea, serotonin-irritation, and sudden infant death syndromes.

Thus, according to a ninth aspect of the present invention, there is provided a method of treating a patient having a chronic abnormally high brain level of 5HT or 5HIAA which comprises administering to the patient an effective 5HT- or 5HIAA- lowering amount of a compound of Formula I or a pharmaceutically acceptable salt thereof. Said amount usually will be in the range 0.1 mg/kg to 20 mg/kg, especially 0.5 to 10 mg/kg.

A tenth aspect of the present invention provides the use of a compound of Formula I or a pharmaceutically acceptable salt thereof in the manufacture of a medicament for the reduction of chronic abnormally high brain levels of 5HT or 5HIAA.

The compounds of Formula I can be administered in various manners to achieve the desired effect. The compounds can be administered alone or in the form of pharmaceutical preparations to the patient being treated either orally or parenterally, for example subcutaneously or intravenously. The amount of compound administered will vary and can be any effective amount. Depending upon the patient and the mode of administration, the quantity of compound administered may vary over a wide range to provide from about 0.1 mg/kg to 20 mg/kg, usually 0.5 mg/kg to 10 mg/kg, of body weight of the patient per dose. Unit doses of these compounds can contain, for example from about 10 mg to 500 mg usually 10 to 100 mg of the compound and may be administered for example from 1 to 4 times daily.

It is believed that the compounds of Formula I lower the brain and peripheral levels of 5HT and its metabolite 5HIAA and hence relieve disorders associated with chronic abnormally high levels of 5HT or 5HIAA in the brain. Accordingly, the compounds of Formula I and their pharmacologically acceptable acid addition salts are useful in the treatment of disorders associated with abnormally high brain levels of 5HT and/or 5HIAA.

The activity of the compounds to lower brain 5HT or 5HIAA levels can be assessed by measuring the concentrations of 5HIAA in homogenates of whole brains in 0.4M perchloric acid from animals treated with the compounds following the method described by J. Wagner et al J. Neurochem., 38 1241 (1982) and comparing the results with those obtained from animals treated with saline. As an illustration the whole brain level of 5HIAA was reduced by 20% 4.5 hours after treating mice with an ip dose of 10 mg/kg of d,l 3-(3-methoxyphenyl)-3-(3''-N,N-dimethylaminopropyl)-4, 4-dimethyl-2,6-dioxopiperidine hydrochloride.

It has further unexpectedly been found that the compounds of Formula I enhance the immune response in mice by a mechanism which probably involves a decreased synthesis of 5HT in the periphery. Hence, the compounds of Formula I are of potential use in combatting bacterial and viral infections in animals and in man.

Thus, according to an eleventh aspect of the present invention, there is provided a method of treating a patient having a bacterial or viral infection which comprises administering to the patient an effective 5HT- or 5HIAA- lowering amount of compound of Formula I or a pharmaceutically acceptable salt thereof. Said amount usually will be in the range 0.1 mg/k to 20 mg/kg, especially 0.5 to 10 mg/kg.

According to a twelfth aspect, the present invention provides the use of a compound of Formula I or a pharmaceutically acceptable salt thereof in the manufacture of a medicament for the treatment of bacterial or viral infections in a patient.

The compounds of Formula I can be administered in various manners to achieve the desired antibacterial or antiviral effect. The compounds can be administered alone or in the form of pharmaceutical preparations to the patient being treated either orally or parenterally, for example subcutaneously or intravenously. The amount of compound administered will vary and can be any effective amount. Depending upon the patient and the mode of administration, the quantity of compound administered may vary over a wide range to provide from about 0.1 mg/kg to 20 mg/kg, usually 0.5 mg/kg to 10 mg/kg, of body weight of the patient per dose. Unit doses of these compounds can contain, for example from about 10 mg to 500 mg usually 10 to 100 mg of the compound and may be administered for example from 1 to 4 times daily.

The activity of the compounds to potentiate the immunoresponse can be determined by measuring, by the method described by Elliott and Rozmann, (*J. Immunol.* 115, 495 (1975), the number of immunoglobin M and G (IgM and IgG) antibody forming spleen cells from mice 3-7 days after immunisation with $5 \times 10^8$ sheep red blood cells, the mice having been pretreated with three daily doses of the compounds. As an illustration the number of IgM antibody forming spleen cells from mice treated with three daily doses of 3-(3'-methoxyphenyl)-3-(3''-N,N-dimethylaminopropyl)-4,4-dimethyl-2,6-dioxopiperidine hydrochloride 10 mg/kg ip was $1128 \times 10^6$ on day 4 after immunization which was 189% above control values.

The compounds of general Formula I have the phenyl moiety substituted in one or both meta positions by methoxy, ethoxy or hydroxy. It is presently preferred that the substituent(s) should be hydroxy or, especially, methoxy. It is also preferred that there should be only one substituent and that when there are two substituents they should be the same.

The amino group of the compounds of Formula I is dimethylamino, diethylamino or methylethylamino with dimethylamino being presently preferred. The amino group is connected to the piperidine ring by a divalent ethylene (i.e. n=2) or trimethylene (i.e. n=3) radical with trimethylene being presently preferred.

The piperidine ring of the compounds of Formula I is substituted in the 4-position with methyl and optionally by one or two further methyl groups in the 4 and/or 5 positions. It is presently preferred that there is one further methyl group in the 4 or 5 position, especially in the 4-position.

Examples of compounds of Formula I include the following:-

3-(3'-methoxyphenyl)-3-(2''-N,N-dimethylaminoethyl)-4,4-dimethyl-2,6-dioxopiperidine 3-(3'-methoxyphenyl)-3-(3''-N,N-dimethylaminopropyl)-4,4-dimethyl-2,6-dioxopiperidine (compound 2979—see later);

3-(3'-methoxyphenyl)-3-(2''-N,N-diethylaminoethyl)-4,4-dimethyl-2,6-dioxopiperidine;

3-(3'-methoxyphenyl)-3-(3''-N,N-diethylaminopropyl)-4,4-dimethyl-2,6-dioxopiperidine;

3-(3'-hydroxyphenyl)-3-(2''-N,N-dimethylaminoethyl)-4,4-dimethyl-2,6-dioxopiperidine;

3-(3'-hydroxyphenyl)-3-(3''-N,N-dimethylaminopropyl)-4,4-dimethyl-2,6-dioxopiperidine;

3-(3'-methoxyphenyl)-3-(2''-N,N-dimethylaminoethyl)-4,5-dimethyl-2,6-dioxopiperidine (compound 2939—see later);

3-(3'-methoxyphenyl)-3-(3''-N,N-dimethylaminopropyl)-4,5- dimethyl-2,6-dioxopiperidine (compound 3181—see later);

3-(3'-ethoxyphenyl)-3-(3''-N,N-dimethylaminopropyl)-4,4-dimethyl-2,6-dioxopiperidine;

3-(3'-ethoxyphenyl)-3-(3''-N,N-diethylaminopropyl)-4,4-dimethyl-2,6-dioxopiperidine;

3-(3', 5'-dimethoxyphenyl)-3-(3''-N,N-dimethylaminopropyl)-4,4-dimethyl-2,6-dioxopiperidine (compound 3222—see later);

3-(3', 5'-dimethoxy)-3-(2''-N,N-dimethylaminoethyl)-4,4-dimethyl-2,6-dioxopiperidine;

3-(3', 5'-dimethoxy)-3-(3''-N,N-dimethylaminopropyl)-4,5-dimethyl-2,6-dioxopiperidine; and 3-(3', 5'-dimethoxy)-3-(2''-N,N-dimethylaminoethyl)-4,5-dimethyl-2,6-dioxopiperidine;

The above compounds may be administered in free base form, as an alkali metal or alkaline earth metal salt or as a pharmaceutically acceptable acid addition salt with the proviso that an alkali metal or alkaline earth metal salt is not normally combined with an acid addition salt except in a layer formulation. Representative acid addition salt forms include organic acid salt forms such as the maleate and methane sulphonate and mineral acid salt forms such as the hydrochloride and perchlorate.

The pharmaceutical formulations in which form the active compounds of the invention will normally be utilized are prepared in a manner well known per se in the pharmaceutical art and usually comprise at least one active compound of Formula I in admixture or otherwise in association with a pharmaceutically acceptable carrier or diluent therefor. For making those formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations may be adapted for enteral or parenteral use and may be administered to the patient in the form of tablets, capsules, dragees, suppositories, syrups, suspensions or the like.

Preferably the compounds of Formula I, and any benzodiazepine agonist or inverse agonist for co-administration therewith, are administered orally in the form of a unit dosage. For co-administration, such as a unit dosage may, if desired, have said active agents separately encompassed therein e.g. in separate layers in a layer tablet. Suitably, each unit dose of compound of Formula I is in the range 25 to 200 mg and each unit dose of benzodiazepine agonist or inverse agonist is in the range of 0.05 to 50 mg.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

Aside from the active agents the compositions may contain pharmaceutically inert organic or inorganic adjuvants, optionally granulating agents, binding agents lubricants, dispersing agents, wetting agents and preservatives. Moreover, the pharmaceutical compositions may contain colouring, flavouring and sweentening substances. Adjuvants for the production of tablets may be e.g. calcium carbonate, lactose micro-crystalline cellulose, mannitol or talc. Starch and alginic acid or micro-crystalline cellulose may be used as granulating and disintegrating agents, starch, polyvinylpyrrolidone and gelatine may be used as binding agents and magnesium stearate, stearic acid, colloidal silica and talc as lubricants. Tablet formulation may be coated or uncoated, the coating having the purpose of delaying the disintegration and absorption in the gastrointestinal tract. Suitable suspending agents for the production of liquid administration forms are e.g. methyl cellulose and sodium alginate. Capsule formulation may contain the active agents on their own or together with an inert solid diluent e.q. calcium phosphate, corn starch, lactose, or mannitol The invention is illustrated in the following non-limiting Examples.

EXAMPLE I

Tablets each having the following composition were prepared by conventional techniques:

|     |                      | mg/tablet |
| --- | -------------------- | --------- |
| (a) | Compound AGN 2979 base | 50      |
| (b) | Lactose              | 51.5      |
| (c) | Maize starch dried   | 45        |
| (d) | magnesium stearate   | 1.5       |

EXAMPLE 2

|     |                           | mg/suppository |
| --- | ------------------------- | -------------- |
| (a) | Compound AGN 2979 HCl     | 20             |
| (b) | Oil of Theobroma (cocoa butter) | 980      |

The compound (a) is powdered and passed through a BS No. 100 sieve and triturated with molten oil of Theobroma at 45° C. to form a smooth suspension. The mixture is well stirred and poured into moulds each of nominal 1 G capacity to produce suppositories.

EXAMPLE 3

Tablet Formulation

|     |                       |       |
| --- | --------------------- | ----- |
| (a) | Compound AGN 2979 base | 100 g |
| (b) | Tranxene              | 10 g  |
| (c) | Wheat starch          | 7 g   |
| (d) | Lactose               | 20 g  |
| (e) | Magnesium Stearate    | 1 g   |

The mixture is compressed into 1000 tablets each weighing 138 mg. Analogously an equal weight of Compound AGN 2939 or 50g of Compound AGN 3222 can be substituted for Compound AGN 2979.

EXAMPLE 4

Pill Formulation

|     |                      | per pill |
| --- | -------------------- | -------- |
| (a) | Compound AGN 2979 HCl | 50 mg   |
| (b) | Diazepam             | 3 mg     |
| (c) | Corn starch          | 45 mg    |
| (d) | Liquid glucose       | 7 ml     |

The pills are prepared by blending the active ingredients (a) and (b) and the corn starch, then adding the liquid glucose with thorough kneading to form a plastic mass from which the pills are cut and formed.

EXAMPLE 5

Gelatine Capsule Formulation

|     |                       | per capsule |
| --- | --------------------- | ----------- |
| (a) | Compound AGN 2979 HCl | 50 mg       |
| (b) | Chlorodiazepoxide HCl | 2.5 mg      |
| (c) | Talc                  | 20 mg       |

A capsule is prepared by passing dry powdered active ingredients (a) and (b) and powdered talc in the above proportions through a fine mesh screen and mixing them well. The powder is then filled into hard gelatin capsules at a net fill of 72.5 mg per capsule.

EXAMPLE 6

Suppository

|     |                           | mg/suppository |
| --- | ------------------------- | -------------- |
| (a) | Compound 2979 HCl         | 20             |
| (b) | Diazepam                  | 1              |
| (c) | Oil of Theobroma (cocoa butter) | 979      |

The compound (a) is powdered and passed through a BS No. 100 sieve and triturated with molten oil of Theobroma at 45° C. to form a smooth suspension. The mixture is well stirred and poured into moulds each of nominal 1 G capacity to produce suppositories.

EXAMPLE 7

This Example illustrates the anxiolytic activity of compounds of Formula I.

Fifty seven male hooded Lister rats (Olac Ltd., Bicester) were tested for exploratory activity in the elevated plus-maze test of Pellow and File (Pharmacol Biochem Behav., 24, 525–529 (1986)). The rats were randomly assigned to a control group (11 rats) or test groups to be injected with 3 mg/kg AGN 2979 (7 rats), 10 mg/kg AGN 2979 (8 rats), 30 mg/kg (8 rats); 60 mg/kg (8 rats), 80 mg/kg (7 rats) or 100 mg/kg (8 rats). Each rat was injected intraperitoneally 30 minutes before testing and the rats were tested in randomised order between 1400 and 1600 h.

Each rat was placed in the central square of the elevated plus-maze and observed by an observer blind to the drug treatment. The number of entries into the open and closed arms and the time spent in each type of arm was recorded. The plus-maze was a cruciform structure having opposed open arms (50×10 cm) and opposed enclosed arms (50×10×40) with open roofs. Overall, AGN 2979 caused a significant elevation in percentage number of open arm entries (F(5,50)=3.51, p 0.01); a significant reduction in the total number of arm entries (F(6,50)=6.3, p 0.0001); but no significant effect in percentage time spent on the open arms (F(6,50)=2.1, p 0.07). The mean percentage number of open arm entries, mean percentage time spent on the open arms, and the mean total number of arm entries are given in Table II below together with the respective standard deviations.

TABLE II

| Dose | % open arm entry | % open arm time | total entries |
|---|---|---|---|
| 0 | 37.5 ± 10.2 | 16.4 ± 12.9 | 11.1 ± 5.4 |
| 3 | 34.8 ± 12.7 | 17.0 ± 12.2 | 13.3 ± 5.3 |
| 10 | 28.8 ± 7.8 | 16.6 ± 7.6 | 13.9 ± 5.1 |
| 30 | 25.3 ± 11.3 | 13.8 ± 11.0 | 10.8 ± 3.3 |
| 60 | 30.9 ± 16.6 | 6.4 ± 5.8 | 6.4 ± 4.6 |
| 80 | 38.1 ± 10.5 | 8.6 ± 6.7 | 5.9 ± 2.8 |
| 100 | 48.8 ± 11.0 | 6.3 ± 3.4 | 4.1 ± 1.4 |

The results indicate that AGN 2979 is anxiolytic at least at an initial single ip dose of 100 mg/kg and sedative at initial single ip doses of 60, 80 and 100 mg/kg. However, it is expected that in a chronic testing anxiolytic activity will be apparent at doses below 100 mg/kg and that the sedative action will cease.

The anxiolytic activity observed is between that previously obtained for chlorodiazepoxide and diazepam and at least as good as that obtained for the pyrazolopyridazine derivative tracazolate and the triazolopyridine CL 218,872 (see Pellow and File, Pharmacol Biochem Behav., 24, 525–529) (1986)).

The sedative effect of AGN 2979 was tested using the Holeboard test (File and Ward: 11, Psychopharmacologia 44, 53–59 (1975)). Forty eight male hooded Lister rats (Olac. Ltd., Bicester) were randomly assigned to a control group (10 rats) or to test groups to be injected with 3 mg/kg AGN 2979 (9 rats); 10 mg/kg (10 rats); 30 mg/kg (9 rats) or 100 mg/kg (9 rats). Each rat was injected intra-peritoneally 30 minutes before testing and the rats were tested in randomised order between 0800 and 1200 h.

Each rat was placed in the centre of the Holeboard and its behaviour automatically recorded by infra-red beam breaks 5 minutes. Overall, AGN 2979 significantly reduced motor activity (F(4,42)=7.3, p 0.001) and the number of head dips (F(4,43)=2.8, p 0.05). There was no significant decrease in the number of rears made (F(4,43)=2.15, p=0.09) or time spent head dipping (F(4,43)=2.4, p=0.06). The mean values and standard derivations (SD) are given in Table III below.

TABLE III

|  | Dose mg/kg | | | | |
|---|---|---|---|---|---|
|  | 0 | 3 | 10 | 30 | 100 |
| Motor Activity* | 334.9 | 351.2 | 330.9 | 279.8 | 224.3 |
| (SD) | (54.9) | (69.3) | (49.8) | (70.8) | (58.4) |

TABLE III-continued

|  | Dose mg/kg | | | | |
|---|---|---|---|---|---|
|  | 0 | 3 | 10 | 30 | 100 |
| Number of Rears | 72.5 | 67.2 | 68.8 | 64.0 | 57.0 |
| (SD) | (9.3) | (9.8) | (10.6) | (15.8) | (14.7) |
| Number of Head-dips | 34.6 | 31.7 | 34.4 | 27.5 | 22.2 |
| (SD) | (7.2) | (7.7) | (9.9) | (14.3) | (6.5) |
| Time Head Dipping (secs) | 31.4 | 31.3 | 39.7 | 28.2 | 21.9 |
| (SD) | (10.5) | (9.7) | (13.3) | 19.3 | 6.3 |

*Number of beam breaks

These results indicate that AGN 2979 is sedative at least at an initial single ip dose of 100 mg/kg. However, the sedative effect is modest compared with that of benzodiazepines. As mentioned above, it is expected that the sedative effect will cease on chronic administration of AGN 2979.

EXAMPLE 8

As an illustrative example showing the efficacy of the combination of the benzodiazepine and a compound of Formula I six hospitalised depressive patients treated with the di-potassium salt of clorazepate (Trade Mark Tranxene) (50 mg/day) and an ineffective amount of Compound AGN 2979 ( 30–150 mg/day) showed no significant reduction in Hamilton anxiety score during 14–28 days. However, eight hospitalised depressives given Tranxene (50 mg/day) together with Compound AGN 2979(200–400 mg/day) had their Hamilton anxiety scores reduced from a mean of 35 to a mean of 6 (84% reduction) during 21–28 days.

EXAMPLE 9

This example illustrates the use of compounds of Formula I in the treatment of sleep apnea. A male subject aged 54 years, height 178 cm and weighing 83 kilograms having persistent awakening episodes of obstructive sleep apnea has been treated with compound AGN 2979 at a daily dose level of 120 mg. Sleep apnea episodes at first decreased in intensity and completely disappeared after one week of treatment. The patient has since remained symptom free for 14 months on a single maintenance dose of 120 mg every four days.

In the Examples above, the active compound was used in the form of the racemate (d,l). However, as is apparent from Formula I herein, AGN 2979 and other compounds of said formula exist as optical isomers. Experimental work to date indicates that the individual isomers are of substantially equal activity in the medical uses to which this application relates.

I claim:

1. A method of treating anxiety which comprises administering to a patient suffering anxiety, an effective anxiolytic amount of Formula I

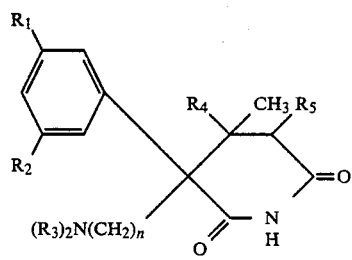

wherein:

$R_1$ represents methoxy, ethoxy or hydroxy,
$R_2$ represents methoxy, ethoxy, hydroxy or hydrogen;
each $R_3$ independently represents methyl or ethyl;
$R_4$ represents hydrogen or methyl;
$R_5$ represents hydrogen or methyl; and
n represents 2 or 3,
or a pharmacologically acceptable acid addition salt thereof.

2. The method of claim 1 in which $R_1$ represents methoxy or hydroxy, $R_2$ represents hydrogen, each $R_3$ represents methyl and n is 3.

3. The method of claim 2, in which $R_4$ represents methyl and $R_5$ represents hydrogen.

4. The method of claim 1 in which the dioxopiperidine in 3-(3'-methoxyphenyl)-3-(3''-dimethyllaminopropyl)-4,4-dimethyl-2,6-dioxopiperidine.

* * * * *